United States Patent [19]
Carr et al.

[11] Patent Number: 5,064,840

[45] Date of Patent: Nov. 12, 1991

[54] ANTI-PSYCHOTIC PIPERIDYLBENZIMIDAZOLE COMPOUNDS

[75] Inventors: Albert A. Carr, Cincinnati; Francis P. Miller, Loveland; John M. Kane, Cincinnati, all of Ohio

[73] Assignee: Merrell Dow Pharmaceuticals, Cincinnati, Ohio

[21] Appl. No.: 511,893

[22] Filed: Apr. 10, 1990

Related U.S. Application Data

[63] Continuation of Ser. No. 389,036, Aug. 3, 1989, abandoned.

[51] Int. Cl.[5] .................. A61K 31/445; C07D 401/02

[52] U.S. Cl. .................... 514/322; 546/199
[58] Field of Search .................. 546/199; 514/322

[56] References Cited

U.S. PATENT DOCUMENTS

| | | | |
|---|---|---|---|
| 4,148,796 | 4/1979 | Yamamoto et al. | 546/199 |
| 4,344,948 | 8/1982 | Takai et al. | 424/251 |

*Primary Examiner*—Mary C. Lee
*Assistant Examiner*—Joseph K. McKane
*Attorney, Agent, or Firm*—J. Michael Dixon

[57] ABSTRACT

The present invention is directed to a new class of therapeutic agent which are useful as anti-psychotic agents and as analgesics.

3 Claims, No Drawings

ANTI-PSYCHOTIC PIPERIDYLBENZIMIDAZOLE COMPOUNDS

This is a continuation of application Ser. No. 389,036, filed Aug. 3, 1989, abandoned.

The present invention is directed to a new class of piperidinyl benzimidazole dopamine antagonists which are useful as anti-psychotic agents and as analgesics. Another aspect of the invention is directed to a method for the treatment of psychotic illnesses and a method for the treatment of pain. An additional aspect of the invention is directed to pharmaceutical compositions containing these agents.

In accordance with the present invention, a new class of therapeutic agents has been discovered which can be described by the following formula:

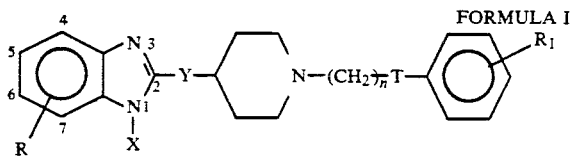

FORMULA I in which Y is represented by CO or CHOH; T is represented by CO or CHOH; X is represented by hydrogen or a $C_{1-6}$ alkyl; n is represented by 3 or 4; R and $R_1$ are each independently represented by hydrogen, $C_{1-6}$ alkyl, $C_{1-6}$ alkoxy, halogen, —OH or —$CF_3$.

These compounds are dopamine antagonists and are thus useful in the treatment of psychotic illnesses such a mania, schizophrenia, etc. The compounds are also analgesics and can be used in the treatment of pain.

As used in this application:
a) the term "halogen" refers to a fluorine, chlorine, or bromine atom;
b) the term "$C_{1-6}$ alkyl" refers to a branched or straight chained alkyl group containing from 1-6 carbon atoms, such as methyl, ethyl, n-propyl, isopropyl, n-butyl, isobutyl, t-butyl, n-pentyl, n-hexyl, etc.;
c) the term "$C_{1-6}$ alkoxy" refers to a straight or branched alkoxy group containing from 1-6 carbon atoms, such as methoxy, ethoxy, n-propoxy, isopropoxy, n-butoxy, isobutoxy t-butoxy, n-pentoxy, n-hexyloxy, etc.;
d) the term "CO" refers to a carbonyl group having the following structure:

e) the term "CHOH" refers to a hydroxymethylene group;
f) the term "ketal" refers to the following substituent:

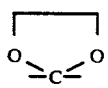

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric and phosphoric acid. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Either the mono- or di-acid salts can be formed, and such salts can exist in either a hydrated or substantially anhydrous form. In general, the acid addition salts of these compounds show increased solubility in water and various hydrophilic organic solvents and which in comparison to their free base forms, often demonstrate higher melting points.

Some of the compounds of Formula I contain asymmetric centers. Any reference in this application to one of the compounds represented by Formula I is meant to encompass either a specific optical isomer or a mixture of enantiomers or diasteriomers. The specific optical isomers can be separated and recovered by techniques known in the art such as chromatography on chiral stationary phases or resolution via chiral salt formation and subsequent separation by selective crystallization.

In the compounds of Formula I wherein R is other than hydrogen, there can be up to 2 such substituents occurring on the indicated benzimidazole ring. These substituents can be the same or can differ. These substituents can be located at any of positions 4, 5, 6, or 7 of the benzimidazole ring. In those compounds in which $R_1$ is other than hydrogen, there can be up to 2 such substituents occurring on the indicated phenyl ring. These substituents can be the same or differ and can be located at any of the ortho, meta, or para positions.

In those compounds of Formula I in which X is represented by a hydrogen atom, the benzimidazole moiety of the compounds of Formula I may exist in two tautomeric forms. This tautomerism produces positional isomers which exist in a state of equilibrium. Those compounds in which X is hydrogen and the phenyl ring of the benzimidazole moiety is substituted with a single non-hydrogen substituent (i.e. R is a mono-halogen atom, mono-alkyl, mono-alkoxy, monohydroxy or mono-trifluoromethyl function) will inherently exist as a mixture of positional isomers in a constant state of equilibrium. These compounds will exist as a mixture of the 4,7- or 5,6- positional isomers due to this tautomeric equilibrium. This tautomeric equilibrium may be depicted as: Any

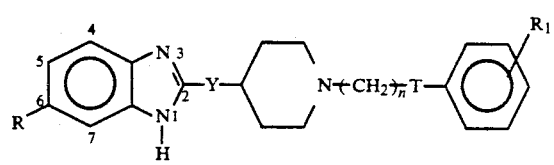

-continued

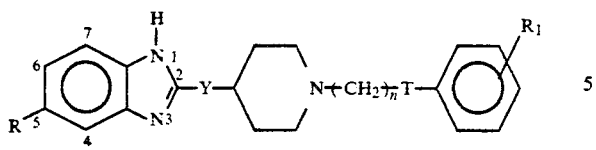

reference to the compounds of Formula I should be considered to encompass any of these tautomers or any the positional isomers which are created by this tautomerism.

It is currently preferred for n to be 3, and for R and R₁ to be represented by either hydrogen or a halogen.

Illustrative compounds encompassed by Formula I include:

a) 4-[4-(1H-benzimidazol-2-yl-carbonyl)-1-piperidinyl]-1-(4-fluorophenyl)-1-butanone
b) 4-[4-[(5-fluoro-1H-benzimidazol-2-yl)carbonyl]-1-piperidinyl]-1-(4-fluorophenyl)-1-butanone
c) 4-[4-[(1,5-dimethyl-1H-benzimidazol-2-yl)carbonyl]-1-piperidinyl]-1-(4-fluorophenyl)-1-butanone
d) 4-[4-[(5-fluoro-1H-benzimidazol-2-yl)carbonyl]-1-piperidinyl]-1-phenyl-1-butanone
e) 5-fluoro-alpha-[1-[4-(4-fluorophenyl)-4-hydroxybutyl]-4-piperidinyl]-1H-benzimidazole-2-methanol
f) 4-[4-[(5-chloro-1H-benzimidazol-2-yl)hydroxymethyl]-1-piperidinyl]-1-(4-fluorophenyl)-1-butanone
g) 4-[4-[(5,6-dichloro-1H-benzimidazol-2-yl)carbonyl]-1-piperidinyl]-1-(4-fluorophenyl)-1-butanone
h) 1-(4-fluorophenyl)-4-[4-[[1-methyl-5-(trifluoromethyl)-1H-benzimidazol-2-yl]carbonyl]-1-piperidinyl]-1-butanone The compounds of Formula I can be synthesized using techniques that are known in the art. One method of preparing these compounds is to first synthesize one of the piperidinyl benzimidazole intermediates described by formula V in which Y is represented by either CO or CHOH.

Those intermediates in which Y is represented by CO can be prepared as shown below in Reaction Scheme I:

REACTION SCHEME I
STEP A

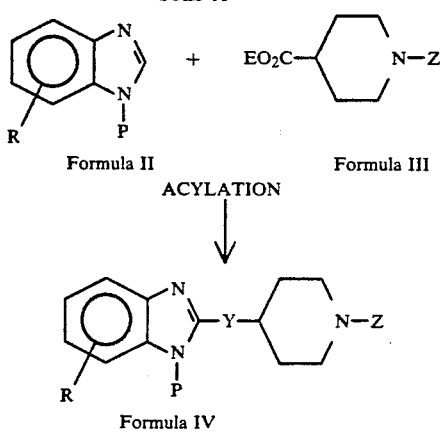

-continued
REACTION SCHEME I
STEP B
DEPROTECTION

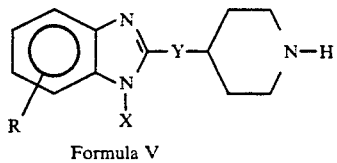

Formula V

In Formula II, R is as in Formula I and P is either a $C_{1-6}$ alkyl or a silane protecting group such as —CH₂—O—(CH₂)₂—Si—(CH₃)₃ (SEM group). A number of other protecting groups may also be utilized, for example, the vinyl, dimethylaminomethyl, and the hydroxymethyl (as its lithio derivative) groupings. In Formula III, E is represented by a $C_{1-6}$ alkyl, preferably methyl or ethyl, and Z is a suitable protecting group such as a t-BOC. In Formula IV, P, Z, and R are as above and Y is represented by CO. In Formula V, X is represented by hydrogen or a $C_{1-6}$ alkyl, R is as in Formula I, and Y is CO.

The initial step in the production of the piperidinyl intermediate of Formula V is to conduct an acylation reaction between a benzimidazole derivative as described by Formula II and a piperidinyl derivative as described by Formula III.

As is apparent to those skilled in the art, it is preferred that the non-reacting substituents of the benzimidazole of Formula II correspond to those appearing in the piperidinyl benzimidazole of Formula I, with the exception of any protecting group which might be present. If X is to be represented by hydrogen in the final product, then one of the protecting groups identified above should be placed on the indicated nitrogen atom prior to the acylation. If X is to be a $C_{1-6}$ alkyl in the desired product, then a protecting group is not necessary.

Methods for producing any of the benzimidazoles of Formula II are known in the art. Typically they are produced by N-alkylating an appropriately substituted benzimidazole with an alkyl halide.

Methods for preparing the protected benzimidazoles of Formula II are well known in the art. For example, the SEM group can be placed on the benzimidazole by contacting it with a 10% molar excess of NaH and then with a molar excess Cl—CH₂—O—(CH₂)₂—Si—(CH₃)₃ for a period of time ranging from 30 minutes to 1 hour. The reaction is typically conducted in an aprotic solvent such as dimethylformamide at a temperature range of from 0° C. to 50° C. The protected benzimidazole of Formula II can be recovered and purified using techniques known in the art, such as, for example Kugelrohr distillation.

In the piperdinyl derivative of Formula III, neither E nor Z will be retained in the final product and thus are not pertinent to the structure of the final product. Methods for producing the piperidinyl derivatives of Formula III are also known in the art.

The acylation reaction between the benzimidazole of Formula II and the piperidinyl derivative of Formula III can be conducted utilizing techniques known in the art. Typically, a solution of the benzimidazole derivative of Formula II will be contacted with an organolithium compound such as n-butyl lithium for a period of time ranging from about 5 minutes to about 30 minutes and more preferably about 15 minutes; at temperature range of from about −90° C. to about −50° C. and more preferably about −78° C. The organolithium compound will be present in the quantity from about 1.0 to about 1.1 equivalents for every mole of benzimidazole derivative utilized, and more preferably be present in an approximately equimolar quantity with the benzimidazole derivative. The reaction is typically conducted in an organic solvent such as, tetrahydrofuran.

The piperidinyl derivative of Formula III is then slowly added to the reaction zone until it is present in an approximately equimolar quantity relative to the benzimidazole derivative and the reaction medium is warmed from about −78° C. to about 0° C. The reaction is allowed to proceed for a period of time ranging from about 20 minutes to about 5 hours, and more preferably about 30 minutes. The reaction is then quenched with a proton source such as, for example, saturated aqueous ammonium chloride or methanol.

The piperidinyl derivative of Formula IV produced by this acylation reaction can be recovered by techniques known in the art such as extraction with ethyl acetate after the addition of water. The desired piperidinyl benzimidazole will be located in the organic phase. The organic phase is typically dried and concentrated prior to its further utilization in the synthesis. It is not necessary that the piperidinyl benzimidazole of Formula IV be purified prior to the deprotection reaction indicated above. If desired, it can be purified by chromatographic techniques known in the art.

The next step in the reaction sequence is to subject the piperidinyl benzimidazole produced above to a deprotection reaction which removes the protecting group represented by Z and the protecting group represented by P, providing P is not a $C_{1-6}$ alkyl.

This deprotection reaction can be conducted utilizing techniques well known in the art. Typically the protected piperidinyl benzimidazole of Formula IV is subjected to a mildly acidic hydrolysis which serves to remove the protecting group or groups present on the molecule. Trifluoroacetic acid is a suitable mild acid and is typically used at a temperature of from 0° C. to room temperature.

The deprotected piperidinyl benzimidazole intermediate of Formula V produced by this hydrolysis can be recovered by techniques known in the art such as extraction with ethyl acetate. The reaction zone is typically neutralized with a base such as sodium bicarbonate prior to extraction. The deprotected piperidinyl benzimidazole will be located in the organic phase. The organic phase is typically dried and concentrated prior to further purification.

The deprotected piperidinyl benzimidazole intermediate of Formula V can be purified if desired according to techniques known in the art. For example, one suitable technique is to subject the concentrate obtained above to flash chromatography utilizing an organic solvent such as ethyl acetate as the eluting agent. The eluent can be evaporated and the resulting product can be recrystallized from a suitable solvent such as, for example, cyclohexane. Other suitable solvent systems will be readily apparent to those skilled in the art.

Those piperidinyl benzimidazole intermediates of formula V in which Y is represented by CHOH can be produced as described in Reaction Scheme II:

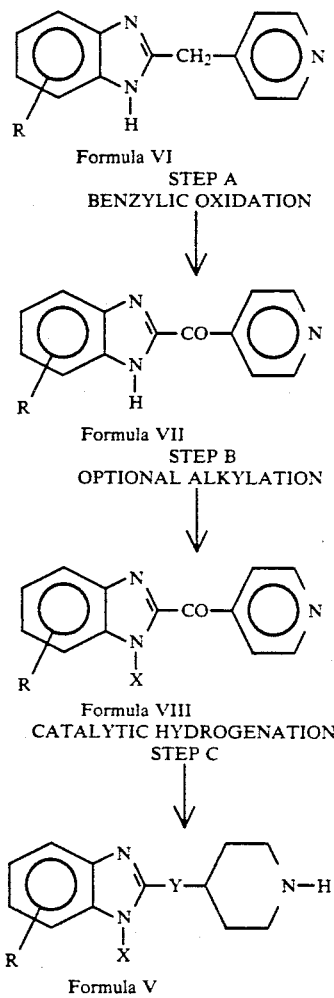

REACTION SCHEME II

Formula VI
STEP A
BENZYLIC OXIDATION

Formula VII
STEP B
OPTIONAL ALKYLATION

Formula VIII
CATALYTIC HYDROGENATION
STEP C

Formula V

In Step A of the reaction, a pyridinyl benzimidazole as described by Formula VI in which R is as in Formula I, is subjected to a benzylic oxidation thereby producing the pyridinoyl benzimidazole of Formula VII. This benzylic oxidation introduces a carbonyl group into the structure at the indicated position. In optional Step B, a $C_{1-6}$ alkyl group is introduced onto the indicated nitrogen atom of the benzimidazole moiety. This alkylation reaction is conducted if such a substituent is desired in the final product of formula I. In Step C, the pyridinyl benzimidazole of Formula VII or VIII is subjected to a catalytic hydrogenation thereby producing the piperidinyl benzimidazole of Formula V in which Y is represented by CHOH. This catalytic reduction transforms the carbonyl group into a hydroxymethylene group and the pyridine substituent into a piperidine substituent.

Methods for producing the pyridinyl benzimidazoles of Formula VI are known in the art. As is apparent to those skilled in the art, it is preferred that the R substituent be identical to that desired in the final product of Formula I.

The benzylic oxidation of the pyridinyl benzimidazole of Formula VI can be conducted using techniques known in the art. Typically the reactant will be contacted with an oxidizing agent such as selenium (IV) oxide in a solution of acetic acid and heated to a temperature range of from about 50° C. to about 70° C. for a period of time ranging from about 10 to 24 hours under an inert atmosphere such as argon. The quantity of oxidizing agent utilized is not critical, but is typically present in the reaction zone in the quantity of from 1-3 equivalents. Any remaining oxidizing agent is removed by filtration, the solution is neutralized and the crude pyridinyl benzimidazole ketone is recovered by extraction with an organic solvent. The resulting organic layer is dried and concentrated. The crude carbonyl containing pyridinyl benzimidazole produced by this oxidation can be used in the next step of the reaction or it can be purified as is known in the art.

The optional N-alkylation of Step B can be carried out using techniques well known in the art. Typically, a solution of the pyridinyl benzimidazole of Formula VII is contacted with a molar excess of sodium hydride. The reactants are stirred together in a solvent such as toluene or DMF at a temperature range of from about room temperature to about 100° C. for a period of time ranging from 0.5 to 5 hours. A molar excess of the appropriate alkyl halide is then added to the reaction zone and the reactants are stirred together at a temperature range of from about room temperature to about 100° C. for a period of time ranging from 0.5 to 24 hours. The reaction is quenched by the addition of water and the pyridinyl benzimidazole of Formula VIII produced thereby can be recovered from the reaction zone by extraction with a solvent such as ethyl acetate and subsequent concentration of the resulting organic layer. It can optionally be purified by chromatography or recrystallization as is known in the art.

The catalytic hydrogenation of the carbonyl containing pyridinyl benzimidazole of Formula VII or VIII can be conducted using techniques known in the art. Typically the compound of Formula VII or VIII is contacted with a catalyst such as platinum or rhodium in an alcoholic solvent. If desired, the catalyst can be on carbon, silica or any other support known in the art. The amount of catalyst utilized is not critical, but is typically present in the quantity of 1 to 20 weight percent. The reaction zone is then charged with 1 to 100 atmospheres of hydrogen and the reaction is allowed to proceed until about 4 equivalents of hydrogen have been consumed. The catalyst is removed by filtration and the product, the piperidinyl benzimidazole of Formula V in which Y is represented by CHOH, is recovered by either extraction or concentration as is known in the art. If desired, the compound can be purified by chromatography or recrystallization as is known in the art.

Those compounds of Formula I in which Y is represented by either CO or CHOH and T is represented by CO can be produced as depicted below in Reaction Scheme III via an N-alkylation reaction between one of the piperidinyl benzimidazole intermediates of Formula V and an alkylene phenyl derivative as described by Formula IX below:

REACTION SCHEME III

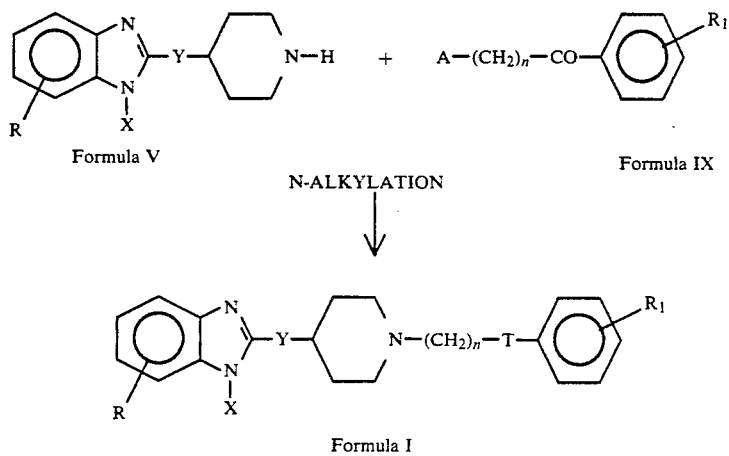

Formula V

N-ALKYLATION

Formula IX

Formula I

In Formula V, R is as defined in Formula I and Y is CO or CHOH depending upon the desired final product. In Formula IX, $R_1$, and n are as in Formula I and A is a halogen atom. The alkylene phenyl derivatives of Formula IX are known in the art as are methods for their production.

As is apparent to those skilled in the art, it is preferred that the non-reacting substituents of the piperidnyl benzimidazole intermediate of Formula V and the alkylene phenyl derivative of Formula IX correspond to those appearing in the final product. For example, if the desired product is 4-[4-(1H-benzimidazol-2-yl-carbonyl)-1-piperidinyl]-1-(4-fluorophenyl)-1-butanone, then it can be produced by conducting an N-alkylation reaction between 4-(2-benzimidazoyl)piperidine and p-fluoro-δ-chlorobutyrophenone.

It may be desirable to place a ketal protecting group on the carbonyl moiety of the alkylene phenyl derivative of Formula IX prior to conducting the N-alkylation reaction. This is especially desirable if $R_1$ is to be represented by fluorine. This ketal protecting group can be placed on the molecule and removed from the product of the N-alkylation reaction using techniques well known in the art.

The N-alkylation depicted above in Reaction Scheme III is accomplished according to techniques known in the art. This N-alkylation reaction is typically conducted in the presence of a base such as $K_2CO_3$, $Na_2CO_3$, $NaHCO_3$, or $KHCO_3$. Typically the base will be present in the reaction zone in a quantity of from about 1 to about 3 equivalents for every mole of piperidinyl benzimidazole utilized.

It is preferred that the piperidinyl benzimidazole intermediate of Formula V and the alkylene phenyl derivative of Formula IX be present in the reaction zone in approximately equimolar quantities. A moderate excess of either reactant is not deleterious to the reaction however. It is also preferred that the reaction be conducted at elevated temperatures. Typically the reactants are stirred together at a temperature range of from about 50° C. to about 100° C. for a period of time ranging from about 30 minutes to about 48 hours. The reaction is also typically conducted in an organic solvent such as dimethylformamide, acetonitrile, dimethyl sulfoxide, benzene, or toluene.

The piperidinyl benzimidazole derivatives of Formula I can be recovered from the reaction zone according to techniques known in the art such as extraction with ethyl acetate after the addition of water. The desired piperidinyl benzimidazole will be located in the organic phase. The organic phase is typically dried and concentrated prior to further purification utilizing conventional techniques.

The piperidinyl benzimidazole can be purified according to techniques known in the art. For example, one suitable technique is to subject the concentrate obtained above to flash chromatography utilizing an organic solvent such as ethyl acetate as the eluting agent. The eluent can be evaporated and the resulting product can be recrystallized from a suitable solvent such as, for example, cyclohexane. Other suitable solvent systems will be readily apparent to those skilled in the art.

Those compounds of Formula I in which Y and T are both represented by hydroxymethylene groups (CHOH) can be produced by the methodology depicted below in Reaction Scheme IV:

REACTION SCHEME IV

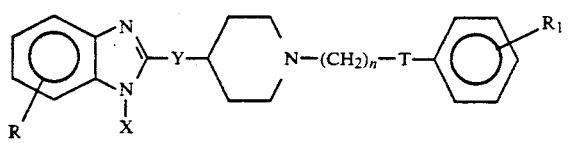

FORMULA I, Y = CO or CHOH, T = CO

-continued
REACTION SCHEME IV
REDUCTION

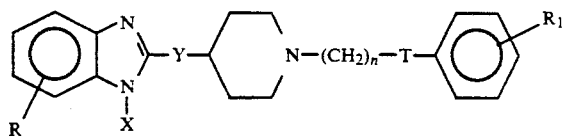

FORMULA I, Y = T = CHOH

A piperidinyl benzimidazole derivative as described by Formula I in which Y is represented by either CO or CHOH, T is represented by CO, and R, $R_1$, and n are as in the desired product, is subjected to a reduction reaction thereby producing the desired piperidinyl derivative of Formula I in which Y and T are both represented by CHOH, as depicted, and R, $R_1$, and n are as defined above. For example if the desired product is alpha-[1-[4-(4-fluorophenyl)-4-hydroxybutyl]-4-piperidinyl]-1H-benzimidazole-2-methanol then it can be produced by reducing 4-[4-(1H-benzimidazol-2-yl-carbonyl)-1-piperidinyl]-1-(4-fluorophenyl)-1-butanone.

The reduction reaction can be carried out utilizing techniques well known in the art. Typically the piperidinyl benzimidazole of Formula I in which Y is represented by CO or CHOH and T is represented by CO, is contacted with a reducing agent such as sodium or potassium borohydride. The reducing agent is generally present in the quantity of from about 1 to about 4 equivalents, and more preferably from 1-2 equivalents. The reduction is conducted at a temperature ranging from room temperature to the reflux temperature of the solvent, more preferably room temperature. The reduction is typically conducted in an alcohol such as methanol, ethanol, or isopropanol.

The reduced piperidinyl benzimidazole can be recovered and purified using techniques analogous to those previously described for the compounds of Formula I in Reaction Scheme III.

Alternatively, the reduction can be conducted by hydrogenation utilizing catalysts such as platinum, ruthenium, etc; according to techniques known in the art.

Those compounds of Formula I in which Y is represented by CO and T is represented by CHOH can also be made utilizing techniques known in the art. One method of producing these compounds is depicted in Reaction Scheme V below:

REACTION SCHEME V

STEP A

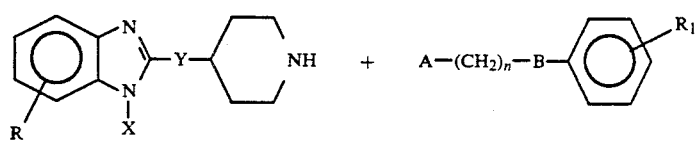

Formula V          Formula X

REACTION SCHEME V
N-ALKYLATION

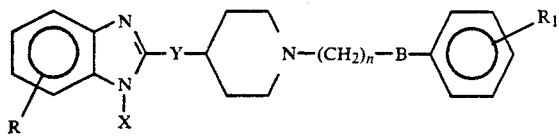

Formula Ia
STEP B
DEPROTECTION

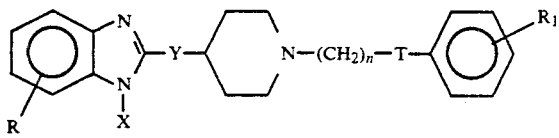

Formula I

A piperidinyl benzimidazole intermediate of Formula V in which Y is represented by CO, X and R are as in Formula I, is N-alkylated with an alkylene phenyl derivative as described by Formula X in which B is represented by a silyl protected hydroxymethylene group, A is a halogen atom, $R_1$ and n are as in Formula I. This N-alkylation produces a protected piperidinyl benzimidazole as depicted by Formula Ia in which R, $R_1$, X and n, are as in Formula I, Y is a carbonyl, and B is a silyl protected hydroxymethylene group. The desired compound of Formula I can then be produced by subjecting the protected piperidinyl benzimidazole of Formula Ia to a deprotection reaction, thereby converting the silane ether protecting group into a hydroxymethylene group and leaving the other substituents unchanged.

The substituents represented by R and X in the piperidinyl benzimidazole starting material of formula V should correspond to those in the desired product of formula I. The non-reacting substituents of the alkylene phenyl derivative of formula X, with the exception of the silane ether protecting group, should correspond to those in the desired product. B can be represented by any suitable silane protecting group. Representative examples of suitable silane protecting groups include t-butyldimethylsilyl or t-butyldiphenylsilyl. Methods for producing the silylated alkylene phenyl derivatives of formula X are known in the art.

For example if the desired compound of Formula I is α-(4-fluorophenyl)-4-[4(2-benzimidazoyl)-1-piperidinebutanol]then the appropriate starting materials are 4-(2-benzimidazoyl) piperidine and 1-(4-fluorophenyl)-1-trimethylsilyloxy-4-chlorobutane.

The N-alkylation reaction between the piperidinyl benzimidazole of Formula V and the silylated alkylene phenyl derivative of Formula X can be conducted in the same manner as the N-alkylation of Reaction Scheme III. The protected piperidinyl benzimidazole of Formula Ia produced thereby can be recovered from the reaction zone using techniques known in the art such as extraction or concentration. This crude product can be subjected to the deprotection reaction depicted above or it can be purified using techniques known in the art such as chromatographic purification or recrystallization from appropriate solvent system.

The deprotection reaction can be conducted using techniques well known in the art. Typically, the silyl ether protecting group is removed by contacting the piperidinyl benzimidazole of Formula Ia with a source of fluoride ions, such as, for example, tetrabutyl ammonium fluoride at room temperature in an aprotic solvent such as tetrahydrofuran.

The piperidinyl benzimidazole of Formula I produced via this deprotection reaction can be recovered from the reaction zone by techniques known in the art such as extraction with ethyl acetate after water has been added to the reaction zone, followed by drying and concentration of the resulting organic phase. The crude piperidinyl benzimidazole of Formula I can be purified by the methods discussed in Reaction Scheme III for purifying the compounds of Formula I.

As with most other organic compounds, the compounds of Formula I as well as the intermediate of Formula V can be produced utilizing other techniques known in the art. For example, those compounds of Formula I in which Y and T are both represented by CHOH can also be produced in the following two step reaction scheme. Initially an N-alkylation reaction is conducted with a piperidinyl intermediate as described by Formula V in which Y is represented by CHOH and a silyated alkylene phenyl derivative as described by Formula X of Reaction Scheme V. This N-alkylation reaction can be conducted in the same manner as the N-alkylation of Reaction Scheme III. This N-alkylation produces a compound which can be described by Formula I in which Y is represented by CHOH, T is a silyl protected hydroxymethylene group and R, $R_1$, and n are as in Formula I. The desired compound of Formula I can then be produced by removing the silyl ether protecting group using the deprotection reaction discussed in Reaction Scheme V. The desired compound of Formula I can be recovered and purified using the techniques taught in Reaction Scheme III above.

The piperidinyl benzimidazole intermediate of Formula V in which Y is represented by CHOH, can also be produced via the alternative reaction scheme depicted below:

REACTION SCHEME VI
STEP A

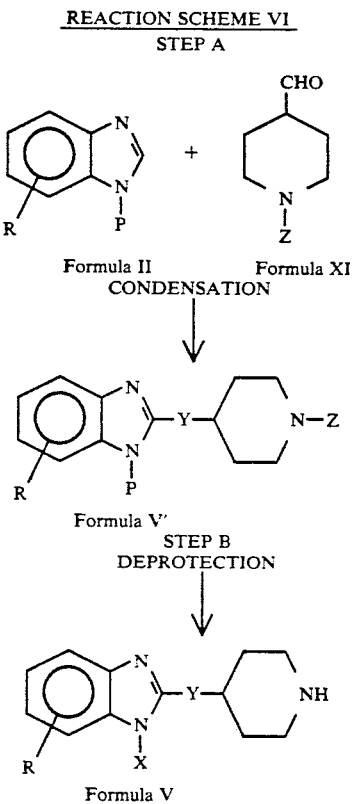

Formula II    Formula XI
CONDENSATION

Formula V'
STEP B
DEPROTECTION

Formula V

A condensation reaction is conducted between a benzimidazole as previously described by Formula II in which R is as in Formula I and P is either $C_{1-6}$ alkyl, a suitable silane protecting group or one of the other protecting groups described in Reaction Scheme I and a piperidinyl aldehyde as described by Formula XI in which Z is a suitable protecting group such as a t-Boc group. This produces a protected piperidinyl benzimidazole as described by Formula V' in which R, P, and Z are as defined above and Y is represented by CHOH. This protected piperidinyl benzimidazole is then subjected to a deprotection reaction which produces the desired piperidinyl benzimidazole intermediate of Formula V in which Y is represented by CHOH.

Methods for producing the benzimidazoles of Formula II and the piperidinyl aldehydes of Formula XI are known in the art. As is apparent to those skilled in the art, it is preferred that the non-reacting substituents of the benzimidazole correspond to those of the desired product. If X is to be hydrogen, then it is necessary to utilize a protected benzimidazole in the condensation reaction. As in Reaction Scheme I, if X is to be represented by a hydrogen atom, a silane protecting group is typically utilized. If X is to be represented by a $C_{1-6}$ alkyl, then it is not necessary to use a protecting group at this position.

The condensation reaction can be conducted using the same methodology taught for the acylation of Reaction Scheme I substituting the piperidinyl aldehyde at Formula XI for the piperidinyl derivative of Formula III. The resulting product can also be recovered and optionally purified in the same manner as well. The deprotection reaction is also conducted in the same manner as as the deprotection reaction carried out in Reaction Scheme I as well as the recovery and optional purification thereafter.

It is also possible to produce those compounds of Formula I in which Y is represented by CHOH and T is represented by either CO or CHOH, utilizing a Reaction Scheme which is analagous to that described immediately above in Reaction Scheme VI. A condensation reaction is conducted between one of the benzimidazoles of Formula II as described in Reaction Scheme VI, and an aldehyde derivative as described by Formula XII:

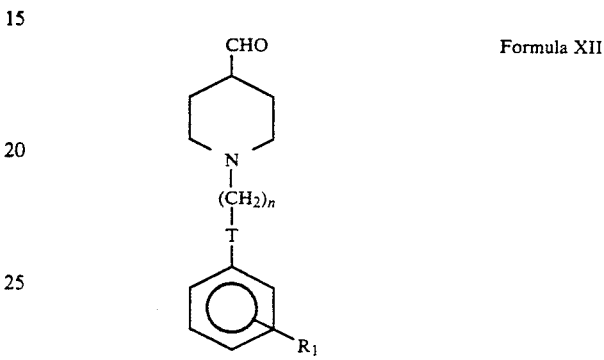

Formula XII in which n and $R_1$ are as in Formula I, and T is a ketal protecting group, when T is to be represented by CO in the final product, and a silyl protected hydroxymethylene group when T is to be represented by CHOH in the final product.

The condensation reaction can be conducted in the same manner as that taught immediately above in Reaction Scheme VI. If P is represented by a silane protecting group or if T is represented by a silyl protected hydroxymethylene group, then these can be removed from the product of the condensation reaction using the appropriate methodologies taught above in Reaction Scheme I and Reaction Scheme V. If T is represented by a ketal protecting group then it can be removed via hydrolysis in the presence of a dilute mineral acid.

As is also apparent to those skilled in the art, the substituent represented by Y in the piperidinyl benzimidazole of Formula V can be manipulated utilizing standard oxidation and reduction reactions as is known in the art. Thus the carbonyl substituent can easily be reduced thereby producing a hydroxymethylene substituent using techniques known in the art. Likewise the hydroxymethylene group can be oxidized into a carbonyl group.

The compounds of Formula I are dopamine antagonists and are useful in the treatment of psychotic illnesses such as schizophrenia, mania, etc. Since the compounds are dopamine antagonists, they will be useful in the treatment of any medical condition for which known dopamine antagonists such as haloperidol or thioridazine are currently prescribed.

One method of demonstrating the anti-psychotic utility of these compounds is by their ability to antagonize the lethality of amphetamine in aggregrated mice. This test is well known in the art as a screening device for detecting anti-psychotic activity.

One method of conducting this test is to cage 20 mice under crowded conditions. A second group is caged under similar conditions to serve as a control. Typically a cage having 29×18×13 cm dimensions is utilized.

Groups of 20 mice are administered vehicle or from 0.01 to 25 mg/kg of test compound intraperitoneally. Approximately 30 minutes later, all groups are administered 20 mg/kg of d-amphetamine sulfate intraperitoneally. Approximately 80% of the control group will expire within 18 to 24 hours. The group receiving the test compound will exhibit a statistically lower incidence of mortality than the control group.

The compounds of formula I also block the effects of serotonin at the serotonin $5HT_2$ receptor. It is believed that these compounds will exhibit a lower incidence of extrapyramidal side effect than other dopamine antagonists which are currently available to clinicians, such as, for example, haloperidol or chlorpromazine.

In order to exhibit these anti-psychotic properties, the compounds need to be administered in a quantity sufficient to antagonize the effect which dopamine has upon dopamine receptors. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their antipsychotic effects at a dosage range of from about 0.01 mg/kg/day to about 25 mg/kg/day. Repetitive daily administration may be desirable and will vary according to the conditions outlined above. Typically, the compounds will be administered from 1-4 times daily.

The compounds of Formula I also exhibit analgesic properties and are useful in the treatment of pain.

One manner of demonstrating the analgesic utility of these compounds is to conduct the following test protocol. Groups of 5 to 10 mice are administered from 1 to 200 mg/kg of the compound either subcutaneously or intragastrically. Thirty minutes after the administration of the test compound, the mice should be administered 0.4 ml of a 0.25% v/v solution of acetic acid intraperitoneally. Five minutes after the administration of the acetic acid, the mice should be observed for signs of squirming and writhing which is indicative of pain. A compound is considered to possess significant analgesic activity if the mice which are administered the compound do not exhibit signs of pain during the test (i.e., squirming and writhing).

The dosage range at which these compounds exhibit this analgesic effect can vary widely depending upon the level of pain the patient is experiencing, the source of the pain, the patient, the particular compound being administered, the route of administration, and the presence of other underlying disease states within the patient, etc. Typically the compounds exhibit their analgesic effects at a dosage range of from about 1 mg/kg/day to about 200 mg/kg/day. Repetitive daily administration may be desirable and will vary according to the conditions outlined above. Typically, the compounds will be administered from 1-4 times daily.

The compounds of the present invention may be administered by a variety of routes. They are effective if administered orally. The compounds may also be administered parenterally (i.e. subcutaneously, intravenously, intramuscularly, intraperitoneally or intrathecally).

Pharmaceutical compositions can be manufactured utilizing techniques known in the art. Typically an antagonistic or analgesic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The compounds may also be admixed with any inert carrier and utilized in laboratory assays in order to determine the concentration of the compounds within the serum, urine, etc., of the patient as is known in the art.

As used in this application:
a) the term "psychosis" refers to a condition where the patient, e.g., a human, experiences a major mental disorder of organic and/or emotional origin characterized by derangement of the personality and loss of contact with reality, often with delusions, hallucinations or illusions. Representative examples of psychotic illnesses which can be treated with the compounds of the present invention include schizophrenia, and mania;
b) the term "treatment" refers to the ability to either relieve or alleviate the patient's disease;
c) the term "analgesia" refers to the either the lack of the normal sensation of pain or a decrease in the normal sensation of pain;
d) the term "patient" refers to warm blooded animals such as, for example, guinea pigs, mice, rats, cats, rabbits, dogs, monkeys, chimpanzees, and humans.

The following examples are presented in order to further illustrate the invention. They should not be construed as limiting the invention in any manner.

EXAMPLE 1

This example demonstrates how to prepare a pyridinyl benzimidazole as described by Formula VI.

A solution of 4-pyridylacetic acid hydrochloride (72.4 g, 417 mmol) and 1,2-phenylenediamine (30.0 g, 277 mmol) was prepared in hydrochloric acid (4.5 M, 550 ml) and refluxed for 17 hours. The cooled solution was slowly added to sodium carbonate (150 g) in water (500 ml). The resulting white solid was filtered and dried to give 47.8 g of a white powder, which was recrystallized from ethyl acetate to afford 2-(4- pyridinylmethyl)-1H-benzimidazole as pale green platelets: m.p. 185-186° C.

EXAMPLE 2

This example demonstrates the preparation of a pyridinyl benzimidazole as described by Formula VII.

A solution of 2-(4-pyridinylmethyl)-1H-benzimidazole (35.0 g, 167 mmol) and selenium (IV) oxide (31.8 g, 287 mmol) was prepared in acetic acid (1.5 l) and stirred for 20 hours under argon at 60° C. The hot solution was filtered through a pad of celite, concentrated, and then slowly neutralized with 5% sodium bicarbonate solution. This aqueous slurry was extracted twice with dichloromethane. The combined organic layers were dried (MgSO4), filtered, concentrated, and the resulting solid recrystallized twice from ethyl acetate to afford 1H-benzimidazol-2-yl-4-pyridinyl-methanone as the desired product as light green needles: m.p. 221-222° C.

EXAMPLE 3

This example demonstrates the preparation of a piperidinyl benzimidazole as described by Formula V.

To stirred ethanol (50 ml) at 0° C. was added acetyl chloride (2.5 ml, 35 mmol) dropwise. After stirring 5 minutes, this ethanolic HCl was added to 1H-benzimidazole-2-yl-4-pyridinyl-methanone (5.0 g, 22.4 mmol) in ethanol (200 ml). This solution was charged with platinum IV oxide (0.5 g) and hydrogen (50 lb/in$^2$) and shaken for 20 hours. The solution was filtered, concentrated, and the resulting solid was recrystallized from methanol with 2-butanone to afford 1H-benzimidazol-2-yl-4-piperidinyl-methanol dihydrochloride as the desired product m.p. 270-272° C.

EXAMPLE 4

The purpose of this example is to demonstrate an N-alkylation between a reduced piperidinyl benzimidazole as described by Formula V and an alkylene phenyl derivative as described by Formula IX.

A solution of 1H-benzimidazole-2-yl-4-piperidinyl-methanol dihydrochloride (5.80 g, 19.1 mmol), 2-(3-chloropropyl)-2-(4-fluorophenyl)-1,3-dioxolane (6.60 g, 27.0 mmol), potassium bicarbonate (5.8 g, 58.0 mmol), and potassium iodide (catalytic amount) was prepared in methylsulfoxide (85 ml) and stirred under argon at 110° C. for 20 hours. The cooled solution was poured into water, and extracted twice with chloroform. The combined organic layers were washed twice with water, dried (MgSO4), and concentrated to an orange oil. The oil was chromatographed on silica gel (75×160 mm), eluting with 10% methanol in chloroform. The appropriate fractions were combined and concentrated to afford α-[1-[3-[2-(4-fluorophenyl)-1,3-dioxolan-2-yl]propyl]-4-piperidinyl]-1H-benzimidazole-2-methanol as the desired product as an off-white solid m.p. 77-79° C.

EXAMPLE 5

The purpose of this example is to demonstrate the oxidation of a hydroxymethylene substituent at the Y position of Formula I into a carbonyl and the hydrolysis of a ketal protecting group.

To a stirred solution of oxalyl chloride (0.51 ml, 0.74 g, 5.8 mmol) in dichloromethane (13 ml) at −78° C. under argon was added dimethylsulfoxide (0.91 g, 12 mmol) in dichloromethane (2.5 ml) at such a rate as to keep the temperature below −50° C. After stirring 20 minutes at −78° C., α-[1-[3-[2-(4-fluorophenyl)-1,3-dioxolan-2-yl]propyl]-4-piperidinyl]-1H-benzimidazole-2-methanol (2.3 g, 5.2 mmol) was added in dichloromethane (20 ml), dropwise, via syringe. After an additional 20 minutes of stirring at −78° C., triethylamine (3.0 ml, 22 mmol) was added, the cooling bath was removed, and the solution was allowed to stir for 1 hour. Water was added, the layers separated, and the aqueous layer extracted with dichloromethane. The combined organic layers were dried (MgSO4), and filtered through a pad of silica (eluting with acetone). The eluent was concentrated to give a white foam. The foam was dissolved in methanol (50 ml), treated with 10% hydrochloric acid, and stirred for 3 hours. The solution was neutralized with 5% sodium bicarbonate, concentrated, and extracted twice with dichloromethane. The combined organic layers were dried (MgSO4), concentrated, and the resulting solid recrystallized from ethyl acetate to afford 4-[4-(1H-benzimidazol-2-yl-carbonyl)-1-piperidinyl]-1-(4-fluorophenyl)-1-butanone as an off-white solid m.p. 155-156° C.

What is claimed is:

1. A method for the treatment of psychosis comprising administering to a patient in need thereof an antipsychotic amount of a compound of the formula:

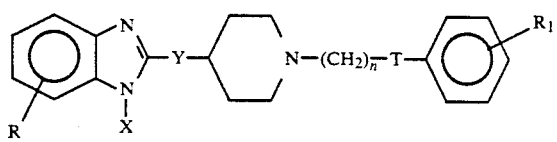

in which Y is represented by CO or CHOH: T is represented by CO or CHOH; X is represented by hydrogen or a $C_{1-6}$ alkyl; n is represented by the integer 3 or 4; R and $R_1$ are each independently represented by hydrogen, $C_{1-6}$ alkyl, $C_{1-6}$ alkoxy, halogen, —OH, or —CF$_3$.

2. A method for antagonizing the effects of dopamine at the dopamine receptor comprising the administration of a compound of the formula:

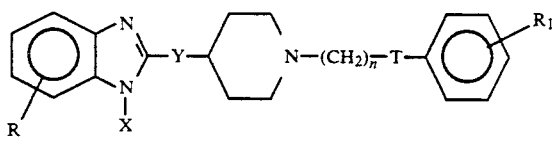

in which Y is represented by CO or CHOH: T is represented by CO or CHOH; X is represented by hydrogen or a $C_{1-6}$ alkyl; n is represented by the integer 3 or 4; R and $R_1$ are each independently represented by hydrogen, $C_{1-6}$ alkyl, $C_{1-6}$ alkoxy, halogen, —OH, or —CF$_3$.

3. A method for producing analgesia comprising administering to a patient in need thereof an analgesic amount of a compound of the formula:

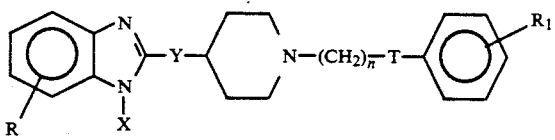

in which Y is represented by CO or CHOH: T is represented by CO or CHOH; X is represented by hydrogen or a $C_{1-6}$ alkyl; n is represented by the integer 3 or 4; R and $R_1$ are each independently represented by hydrogen, $C_{1-6}$ alkyl, $C_{1-6}$ alkoxy, halogen, —OH, or —CF$_3$.

* * * * *